(12) United States Patent
Mett

(10) Patent No.: US 12,270,800 B2
(45) Date of Patent: Apr. 8, 2025

(54) ELECTROCHEMICAL GAS SENSOR

(71) Applicant: Dräger Safety AG & Co. KGaA, Lübeck (DE)

(72) Inventor: Frank Mett, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 649 days.

(21) Appl. No.: 17/555,970

(22) Filed: Dec. 20, 2021

(65) Prior Publication Data

US 2022/0196622 A1 Jun. 23, 2022

(30) Foreign Application Priority Data

Dec. 21, 2020 (DE) .................. 102020134465.1

(51) Int. Cl.
*G01N 27/407* (2006.01)
*G01N 27/404* (2006.01)
*G01N 33/00* (2006.01)

(52) U.S. Cl.
CPC ..... *G01N 33/0036* (2013.01); *G01N 27/4045* (2013.01); *G01N 27/407* (2013.01)

(58) Field of Classification Search
CPC ........... G01N 33/0036; G01N 33/0052; G01N 27/407; G01N 27/4045
See application file for complete search history.

(56) References Cited

U.S. PATENT DOCUMENTS

| | | | |
|---|---|---|---|
| 4,406,770 A * | 9/1983 | Chan | G01N 33/0011 204/406 |
| 5,322,602 A | 6/1994 | Razaq | |
| 2007/0227909 A1* | 10/2007 | Sommer | B82Y 15/00 205/785.5 |
| 2008/0035493 A1 | 2/2008 | Sommer et al. | |
| 2010/0012494 A1 | 1/2010 | Kiesele et al. | |
| 2011/0290671 A1 | 12/2011 | Mett et al. | |
| 2017/0059509 A1* | 3/2017 | Sommer | G01N 33/0052 |
| 2018/0023201 A1 | 1/2018 | Dominguez et al. | |

FOREIGN PATENT DOCUMENTS

| | | |
|---|---|---|
| CN | 105980844 A | 9/2016 |
| CN | 111051866 A | 4/2020 |
| DE | 102006014714 B3 | 5/2007 |
| DE | 102006014715 B3 | 6/2007 |
| DE | 102006014713 B3 | 11/2007 |
| DE | 102014002500 A1 | 8/2015 |
| EP | 2226627 A1 | 9/2010 |
| GB | 2129562 B | 11/1985 |
| JP | H102878 A | 1/1998 |
| WO | 1999/001758 A1 | 1/1999 |
| WO | 2002/031485 A1 | 4/2002 |

* cited by examiner

*Primary Examiner* — Alexander S Noguerola
(74) *Attorney, Agent, or Firm* — McGlew and Tuttle, P.C.

(57) ABSTRACT

An electrochemical gas sensor, for acid analyte gases, has an absorbent, which is suitable for absorbing a reaction product formed at the electrode. The electrochemical gas sensor further has a boron 5 compound, which is suitable for reacting chemically with the acid analyte gas. A process determines the concentrations of acid gases. A process uses an electrochemical gas sensor for determining the concentrations of acid gases.

17 Claims, 2 Drawing Sheets

ELECTROCHEMICAL GAS SENSOR

CROSS REFERENCE TO RELATED APPLICATIONS

This application claims the benefit of priority under 35 U.S.C. § 119 of German Application 10 2020 134 465.1, filed Dec. 21, 2020, the entire contents of which are incorporated herein by reference.

TECHNICAL FIELD

The present invention pertains to an electrochemical gas sensor with an absorbent and with a boron compound, which gas sensor has an improved long-term signal stability compared to gas sensors known from the state of the art in case of admission of acid analyte gases. The present invention further pertains to the use of a gas sensor according to the present invention for measuring acid analyte gases, especially for determining the concentration of hydrogen fluoride as well as to a process for measuring the concentration of acid analyte gases with an electrochemical gas sensor.

TECHNICAL BACKGROUND

Electrochemical gas sensors are generally known from the state of the art. Such gas sensors usually have a working electrode (also called measuring electrode), a counterelectrode (also called auxiliary electrode) and optionally a reference electrode and a protective electrode. These electrodes are usually enclosed by a sensor housing and are in contact with a usually liquid electrolyte. The working electrode and the counterelectrode are usually separated by separators, which are permeable to electrolytes and impermeable to gases. The working electrode and the counterelectrode are in conductive contact with the electrolyte and thus form a galvanic cell (electrochemical measuring cell).

Electrochemical gas sensors are used in many applications, for example, for detecting toxic gases in industrial plants, in production sites, at pipelines, in material storage facilities and in process monitoring in the chemical industry and are used, among other things, as stationary or also portable gas sensors. Electrochemical gas sensors are used especially for the early detection of a critical concentration of toxic and/or explosive gases in order to generate a timely warning against an imminent risk. Further, electrochemical gas sensors are used to detect and to measure acid gases, i.e., gases that have a pH value lower than 7 in an aqueous solution, as they are generated, among other things, in the production of aluminum, in uranium processing, in the semiconductor industry and in the manufacture of semiconductors or even when electric vehicles catch fire. Acid gases are generally defined as gases that have a pH value below 7 on dissolution in or discharge into water. These include, among other things, hydrogen fluoride (hydrofluoric acid, HF), hydrogen chloride (hydrochloric acid, HCl), hydrogen bromide (HBr) or also hydrogen sulfide ($H_2S$) and sulfur dioxide ($SO_2$).

GB 2129562 B discloses the electrochemical detection of hydrogen fluoride (HF), in which platinum wires are used as electrodes. A mixture of calcium bromide and calcium bromate is used as the electrolyte. This presents the particular drawback of a temperature dependence of the detection method.

The use of a measuring electrode made of an electrochemically active metal oxide powder is known from WO 2002/031485 A1. Such metal oxide powders may, however, have high cross sensitivities to other gases, as a result of which low concentrations of the target gas cannot always be reliably detected.

WO 1999/001758 A1 discloses an electrochemical sensor, which is especially suitable for detecting HCl. The working electrode in this sensor has an electrochemically active surface consisting of gold. This will, however, dissolve over time, which may lead to the failure of the sensor in the worst case.

DE 102014002500 A1 discloses an electrochemical gas sensor for acid gases with an absorbent, which is suitable for reacting with a reaction product. Especially barium carbonate ($BaCO_3$), which can react with HF to form barium fluoride and carbonic acid according to the following reaction equation: $2\ HF+BaCO_3 \rightarrow BaF_2+H_2CO_3$, is disclosed as a possible absorbent. It is, however, disadvantageous in the case of the sensor being proposed that the long-term signal stability is compromised when this sensor is used for the measurement or the detection of acid gases, especially HF. This becomes noticeable, among other things, by the fact that the measured signals of the electrochemical gas sensor being proposed have signals dropping to a lower value, which distort the measurement result or do not represent it correctly after a certain use time in case of a change of gas from air to a testing gas containing HF or analyte gas. This is, however, undesirable and compromises the measurement result and hence also the costs for maintenance and replacement of the sensor.

SUMMARY

Therefore, there continues to be a need for electrochemical gas sensors, which can be used especially for the measurement or for the detection of acid gases, and which can have a long-term signal stability, i.e., a reliable measurement result over a long time period, without the measurement result "dropping" to lower measured values, i.e., being distorted, after a certain use time.

An object of the present invention is thus to provide an electrochemical gas sensor, which avoids the problems known from the state of the art. An electrochemical gas sensor shall thus be provided, which is suitable for the measurement or for the detection of acid gases, for example, hydrogen fluoride (HF), hydrogen chloride (HCl), hydrogen bromide (HBr), hydrogen iodide (HI), hydrogen sulfide ($H_2S$), sulfur dioxide ($SO_2$) and acetic acid (AcOH) and other gases, which has long-term signal stability without the measured signals "dropping" or becoming inaccurate after a certain time, and which has a high long-term resistance to gas exposure, i.e., a high long-term signal stability ideally even over a time period of at least 12 months to 18 months. In addition, the object of the present invention is to provide an electrochemical gas sensor, which can be operated by the end user in a cost-effective manner without the gas sensor requiring a high intensity of maintenance or a plurality of maintenance cycles.

Another object of the present invention is to provide a process for measuring or for determining the concentration of acid gases, with which process a higher accuracy can be achieved especially over a time period of at least 12 months to 18 months, without a so-called signal drift, which leads to a distortion of the measurement results, occurring.

It was surprisingly found that the long-term signal stability and hence the measurement accuracy of an electrochemical gas sensor for acid gases, i.e., for gases that have a pH value below 7 in an aqueous solution, can be markedly improved over a long gas exposure time period in case of a simultaneous use of a boron compound in addition to an absorbent.

An electrochemical gas sensor, which has a housing with a working electrode and with a counterelectrode, which are arranged therein, an electrolyte, which is in conductive contact with the working electrode and with the counterelectrode, as well as an absorbent, wherein the absorbent is suitable for absorbing a reaction product formed at the working electrode or a reaction product formed at the counterelectrode. Furthermore, the electrochemical gas sensor according to the present invention has a boron compound, which is suitable for reacting chemically with an acid analyte gas passing through the gas sensor.

Furthermore, a process for determining the concentration of acid analyte gases, with which a high long-term signal stability is guaranteed, is proposed. The process comprises in this case the admission of the acid analyte gas to the gas sensor, wherein the acid analyte gas is reduced at the working electrode and the migrating reaction products are oxidized at the counterelectrode. The acid analyte gas reacts chemically with a boron compound arranged in the gas sensor and the reaction products formed at the counterelectrode are absorbed by an absorbent.

Furthermore, the use of an electrochemical gas sensor for the measurement or for the determination of the concentration of acid gases, especially halogen-containing gases, such as HF, is a part of the present invention.

The analyte gas is the gas which is admitted to the electrochemical gas sensor. The analyte gas has a pH value lower than 7 in an aqueous solution and is also called acid gas in the sense of the present invention. The analyte gas usually diffuses together with air from the ambient atmosphere to the gas sensor according to the present invention and the analyte gas is thus admitted to the electrochemical gas sensor according to the present invention. The analyte gas is an acid gas in an aqueous solution and it may also comprise acid vapors, for example, acetic acid or both, and it comprises in this case hydrogen halides and/or hydrogen sulfide or sulfur dioxide, i.e., the analyte gas may contain, for example, halogen and/or sulfur and/or hydrogen atoms. The analyte gas is preferably a hydrogen halide, for example, hydrogen fluoride (HF), hydrogen chloride (HCl), hydrogen bromide (HBr), hydrogen iodide (HI) or else hydrogen sulfide ($H_2S$), sulfur dioxide ($SO_2$) and acetic acid (AcOH) or mixtures thereof, preferably hydrogen halides such as HF, HCl, HBr and/or HI or mixtures, especially preferably HF. The analyte gas is typically comprised by or contained in the ambient atmosphere of the gas sensor, but it may also be fed to the gas sensor separately, e.g., in well-defined doses, batchwise.

The housing of the electrochemical gas sensor defines this electrochemical gas sensor to the outside. The housing is usually in contact outwards with the ambient atmosphere and forms in the interior of the housing a receiving structure for the electrodes such as the working electrodes, the counterelectrode and optionally a reference electrode and/or a protective electrode as well as for the electrolyte. The housing may be manufactured from different materials typical for the use of electrochemical gas sensors. These include, for example, plastics, for example, polyethylene (PE), polypropylene (PP), perfluoroalkoxy polymers (PFA), fluoroethylene propylene (FEP) or polytetrafluoroethylene (Teflon; PTFE). The housing of the electrochemical gas sensor has, furthermore, an electrolyte reservoir for receiving the electrolyte.

In the gas sensor according to the present invention, the analyte gas diffuses in one embodiment from the ambient air through a hydrophobic (water-repellent) membrane into the electrochemical gas sensor and reaches the three-phase boundary, which is formed by the working electrode, by the electrolyte as well as by the analyte gas. The analyte gas finally reacts at the working electrode (direct reaction), and the reaction products formed at the counterelectrode (reverse reaction) will finally enter the electrolyte again and flow out of the electrochemical gas sensor again. Sensors that operate analogously to this principle (reduction at the working electrode and oxidation at the counterelectrode) are colloquially also called pumping sensors. Pumping sensors are used mainly for the detection of oxygen ($O_2$), ammonia and/or hydrogen halides.

Other electrochemical gas sensors known from the state of the art operate such that the analyte gas diffusing into the gas sensor is oxidized at the working electrode (for example, carbon monoxide into carbon dioxide or hydrogen sulfide into sulfuric acid) and is reduced again at the counterelectrode.

In the simplest case, the housing has an opening for gas exchange with the environment and an electrolyte-filled reaction space, in which the electrodes are arranged. The analyte gas diffuses in this embodiment, for example, through the opening and optionally through a measuring electrode membrane into the reaction space of the gas sensor and further to the working electrode. A direct reaction takes place at the working electrode. It is also possible in another embodiment that the housing has both a gas inlet and a gas outlet, in which case the diffusion path leads from the gas inlet to the working electrode and from the counterelectrode to the gas exchange. It is possible in this embodiment that the gas formed at the counterelectrode diffuses through the electrolyte and optionally through a membrane out of the gas sensor via the gas outlet.

The absorbent according to the present invention is configured such that it can react with at least one reaction product formed at the counterelectrode and/or at the working electrode, preferably with a reaction product formed at the counterelectrode. The absorbent may also comprise other constituents or additives and/or binding agents, for example, Teflon (polytetrafluoroethylene; PTFE), cellulose, cotton and/or polymer fibers, which are suitable especially for arranging the absorbent within the housing of the electrochemical gas sensor and/or in the vicinity of the electrodes, especially of the counterelectrode. The absorbents may thus be carried, for example, on a polymer nonwoven or on a glass nonwoven or be also arranged at the working electrode and/or at the counterelectrode. The absorbent is preferably arranged on or is applied preferably to the counterelectrode, so that the reaction products formed at the counterelectrode can be directly absorbed or captured in this manner directly at the counterelectrode. The absorbent may comprise Teflon in a preferred embodiment.

In another preferred embodiment, the absorbent additionally comprises pulp. This is a suspension, which comprises, for example, water and glass fibers, and which can be manufactured in a cost-effective manner and can especially be shaped and is dimensionally stable. As an alternative pulp, suspensions of cellulose, cotton and/or polymer fibers may be used. Aggregates, such as clay or chalk, may additionally be added to the pulp in some embodiments. Pulp is especially suitable for being mixed with the absorbent. The absorbent is frequently dimensionally unstable and cannot be shaped or can be shaped with difficulty only because it is amorphous and/or crystalline or liquid, more or less able to be shaped. Pulp with the absorbent is advantageous because the pulp makes the absorbent dimensionally stable and the absorbent can be shaped thereby to some extent. It is thus possible, in particular, to mix absorbent with an aqueous pulp, to introduce the mixture into a predefined mold, and to incorporate in this mold an electrically conductive electrode material, for example, carbon fibers, carbon nanotubes (CNT), graphene, graphene oxide, glassy carbon, reduced graphene oxide (rGO), diamond-like carbon (DLC). This is especially preferred because the absorbent can be carried or arranged in this manner directly at the electrode, preferably at the counterelectrode. The absorbent, the glass fibers of the pulp and the electrode material, preferably carbon nanotubes, yield after drying a composite material, which is preferably used as an electrode. It is also possible in another embodiment to carry absorbent directly at the electrode material.

If HF is used as the analyte gas, fluoride anions are formed at first at the working electrode (reduction), and these anions are then oxidized again into HF at the counterelectrode. However, release of HF from the gas sensor is not usually desired because this is, among other things, highly toxic and corrosive. An accumulation or enrichment of HF within the electrochemical gas sensor is likewise undesired, because an accumulation of HF in the interior of the sensor may lead to a so-called sensor drift, which has the consequence that the measurement results will become inaccurate or they will be distorted. It is therefore advantageous if the HF formed at the counterelectrode can react with the absorbent. In a preferred embodiment, the absorbent is selected to be such that the HF formed at the counterelectrode is reacted into a poorly soluble solid or into a solid precipitating in the electrolyte.

The absorbent may also be arranged at a point of the housing or at a plurality of points of the housing of the electrochemical gas sensor. Thus, the absorbent is carried in one embodiment on a polymer nonwoven and the polymer nonwoven, a carrier of the absorbent, is then arranged within the gas sensor. The absorbent is preferably arranged (positioned), as was already described above, in the vicinity of the working electrode or in the vicinity of the counterelectrode, especially preferably in the vicinity of the counterelectrode.

In another embodiment the absorbent is arranged as a plug in the gas outlet. The absorbent can thus form a filter, through which the gas flowing out of the gas sensor must flow or diffuse. The absorbent can then react with the reaction product formed at the working electrode or at the counterelectrode, especially at the counterelectrode, so that a release into the environment can be effectively prevented from occurring. At the same time, the absorbent may in this case form an outer limitation of the electrolyte-filled reaction space. The absorbent is preferably selected such that a compound, which is formed with the reaction product at the counterelectrode, is formed, which is poorly soluble especially in the electrolyte and precipitates in the electrolyte.

In a preferred embodiment, the absorbent comprises a carbonate compound or consists of this, the carbonates being especially alkali carbonates and/or alkaline earth carbonates, and the carbonate is preferably calcium carbonate and/or barium carbonate, especially preferably barium carbonate. HF formed at the counterelectrode can in this case be absorbed according to the following reaction equation: $2 HF + BaCO_3 \rightarrow BaF_2 + H_2CO_3$. Barium fluoride is poorly soluble in the electrolyte. Even though the precipitating barium fluoride is attached at the counterelectrode, it does so without poisoning the counterelectrode (i.e., without clogging the surface of the electrode and hence sealing it for further reaction).

For detecting acid gases (which have a pH value lower than 7 in an aqueous solution), especially hydrogen halide gases, it is advantageous if the electrolyte is a component that contains an organic solvent and a conductive salt, preferably a composition that contains an organic solvent, which contains a quinoid system, for example, from the group of the quinones, and a conductive salt, which has an organic cation.

The conductive salt may be, for example, an ionic liquid. The anion of the conductive salt is in this case preferably selected from the group containing halide, carbonate, sulfonate, phosphate and/or phosphonate, preferably an anion selected from the group containing alkyl sulfonate, alkenyl sulfonate, aryl sulfonate, alkyl phosphate, alkenyl phosphate, alkenyl phosphonate, aryl phosphate, substituted alkyl sulfonate, substituted alkenyl sulfonate, substituted aryl sulfonate, substituted alkyl phosphate, substituted alkenyl phosphate, substituted aryl phosphate, halogenated phosphate, halogenated sulfonate, halogenated alkyl sulfonate, halogenated alkenyl sulfonate, halogenated aryl sulfonate, halogenated alkyl phosphate, halogenated alkenyl phosphate, halogenated aryl phosphate, especially preferably an anion selected from the group containing fluorophosphate, alkyl fluorophosphate, aryl sulfonate, especially preferably from the group containing perfluoroalkyl fluorophosphate, and toluene sulfonate.

It is advantageous in this connection if the conductive salt contains metal ions, onium ions or a mixture of metal ions and onium ions as cations. For example, the metal ions may be selected from among alkali metal ions or alkaline earth metal ions, preferably from among Li, K and/or Na. It is favorable if the onium ions are selected from among ammonium, phosphonium, guanidinium cations and heterocyclic cations, preferably selected from among alkyl ammonium cations and heterocyclic cations, especially preferably selected from among alkyl ammonium, imidazolium and/or substituted imidazolium ions, wherein the substituted imidazolium ions preferably have a structure corresponding to

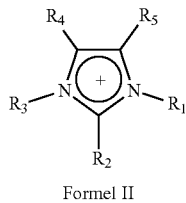

Formula II

Formel II in which R1, R2, R3, R4 and R5 may be selected, independently from one another, from among —H, straight-chain or branched alkyl containing 1 to 20 C atoms, straight-chain or branched alkenyl containing 2 to 20 C atoms or with one or more double bonds, straight-chain or branched alkinyl containing 2 to 20 C atoms and with one or more multiple triple bonds, saturated, partially or fully unsaturated cycloalkyl containing 3-7 C atoms, which may be substituted with alkyl groups containing 1 to 6 C atoms, saturated, partially or fully unsaturated heteroaryl, heteroaryl-C1-C6-alkyl or aryl-C1-C6-alkyl, wherein R2, R4 and R5 are H and R1 and R3 are, each independently from the other, a straight-chain or branched alkyl containing 1 to 20 C atoms.

It may be provided, for example, in particular, that tetrabutylammonium toluene sulfonate or 1-hexyl-3-methylimidazolium-tris(pentafluoroethyl)-trifluorophospharte is used as the conductive salt. Thus, it is especially advantageous if the electrolyte is a mixture of a solvent, a conductive salt and/or an organic mediator, alkylammonium toluene sulfonate and ionic liquids, with a perfluoroalkyl fluorophosphate anion.

Furthermore, it is favorable if the organic mediator is a polyhydroxyl compound, which forms a quinoid system or a naphthalene system on oxidation. For example, the organic mediator may be selected from the group containing ortho-dihydroxybenzene, para-dihydroxybenzene, substituted ortho-dihydroxybenzenes and substituted para-dihydroxybenzenes, dihydroxynaphthalene, substituted dihydroxynaphthalene, anthrahydroquinone, substituted anthrahydroquinone, preferably 1,2-dihydroxybenzene, 1,4-dihydroxybenzene, naphthohydroquinone, substituted 1,2- or 1,4-dihydroxybenzene, substituted hydroquinone, substituted naphthohydroquinone, substituted anthrahydroquinone, especially preferably substituted hydroquinone, and substituted 1,2-dihydroxybenzene. It is especially favorable in this connection if the substituents of the substituted anthraquinones, substituted 1,2-dihydroxybenzene and/or substituted 1,4-hydroquinone are selected from the group containing sulfonyl, tert-butyl, hydroxyl, alkyl, aryl, preferably and/or tert.-butyl.

The boron compound according to the present invention is selected such that it can react chemically with the analyte gas. Boron compound in the sense of the present invention is defined as a compound which contains at least one boron atom. These include all boron compounds that can react chemically with acid gases, i.e., with gases that have a pH value lower than 7 when they are dissolved in water. The boron compound of the electrochemical gas sensor according to the present invention is especially boric acid ($H_3BO_3$) and/or boron trioxide ($B_2O_3$). The boron compound is arranged in the housing of the electrochemical gas sensor according to the present invention. In a preferred embodiment, the boron compound is arranged in a separator layer between the working electrode and the counterelectrode. The working electrode and the counterelectrode are preferably separated from one another by means of a separator layer or by means of a separator material for avoiding electrical short-circuits. All the materials known from the state of the art may be used as separator material. Glass nonwovens and/or polymer nonwovens, which are semipermeable, are preferably used according to the present invention. It is also possible to use electrolyte-impermeable separator layers, so-called semipermeable membranes.

The boron compound may be, among other things, in the form of a powder or tablets. In another embodiment, the boron compound is arranged as a paste in the gas sensor. In yet another embodiment, the boron compound is present as borosilicate glass. Borosilicate glass comprises, among other things, silicon dioxide, boron trioxide, alkali oxides, alkaline earth oxides as well as aluminum oxide. The boron compound is carried in the preferred embodiment on a nonwoven. Among other things, plastic nonwovens and/or glass nonwovens may be used for this purpose. It is thus possible to dissolve the boron compound in a suitable solvent and then to impregnate a polymer nonwoven and/or a glass nonwoven with this solution. A polymer nonwoven or glass nonwoven impregnated in this manner with the boron compound can be used directly in the electrochemical gas sensor. In another embodiment, the impregnated nonwoven is first dried and is then arranged in the gas sensor, especially between the working electrode and the counterelectrode. The polymer nonwovens used are preferably those prepared from polypropylene and/or polyethylene, especially those prepared from polypropylene.

The boron compound may be arranged, in principle, at different points within the housing, and it is preferably arranged between the working electrode and the counterelectrode. It was found to be advantageous, in particular, if the boron compound is located in a separator layer or is carried on this separator layer, and this separator layer is arranged between the working electrode and the counterelectrode. The separator layer comprises especially nonwovens, such as glass nonwovens and/or plastic nonwovens or the separator layer consists of said nonwovens, which act at least partially as carriers for the boron compound.

Without being bound to the theory, the inventor suspects that the signal improvement effect achieved compared to the gas sensors known from the state of the art or the improved long-term signal stability arises due to the fact that the analyte gas, in this case hydrogen fluoride, reacts with boric acid, so that the ions formed at the working electrode can migrate to the counterelectrode according to the following reaction equation: $4\ HF + H_3BO_3 \rightarrow [H] + [BF_4]^- + 3\ H_2O$.

The working electrode and the counterelectrode may be manufactured from the same material or from different materials known to the person skilled in the art, for example, from carbon fibers or from precious metals, such as gold, platinum and/or iridium. The working electrode preferably comprises electrically conductive carbon fibers, especially preferably carbon nanotubes (CNT), graphene and/or diamond-like carbon (DLC) and the working electrode especially preferably comprises reduced graphene oxide (rGO).

The counterelectrode preferably comprises carbon fibers, especially preferably graphene and/or glassy carbon and especially preferably carbon nanotubes (CNT).

The absorbent is preferably arranged at the counterelectrode. It is especially preferred in this connection to arrange carbon nanotubes in an aqueous pulp, in which case the aqueous pulp is mixed with one or more absorbents. A composite material comprising carbon nanotubes as electrode material, absorbent and glass fibers is thus obtained after drying the aqueous pulp. This is especially advantageous because the absorbent is carried or arranged in this manner directly at the counterelectrode in order to absorb and thus to "trap" there the reaction product formed, e.g., HF, i.e., HF formed at the counterelectrode is not released into the ambient atmosphere. In another embodiment, an open-pore carbon sponge is used as the counterelectrode. It is advantageous in this embodiment if the absorbent is introduced at least partially into the pores of the carbon sponge.

An electrochemical gas sensor according to the present invention comprises in an especially preferred embodiment, in addition to a housing and an electrolyte, a working electrode, which is formed from reduced graphene oxide as the electrode material, and a counterelectrode, which is formed from carbon nanotubes as the electrode material. The carbon nanotubes are especially preferably arranged in this embodiment in a composite material comprising glass fibers and barium carbonate, which is used as an absorbent. A nonwoven acting as a carrier for boric acid is arranged as a separator material between the working electrode and the counterelectrode in this embodiment.

In another embodiment, the electrochemical gas sensor according to the present invention also has a reference electrode and/or a protective electrode, and the gas sensor preferably has both a protective electrode and a reference electrode. A reference electrode (reference electrode or comparison electrode) is an electrode with a constant equilibrium potential, which becomes established rapidly and reproducibly. A reference electrode is used as a reference point for the measurement of relative potentials of other electrodes. A protective electrode prevents, e.g., interfering substances from the electrolyte space from diffusing to the working electrode, which may lead to incorrect signals at the working electrode. Interfering substances may be, for example, impurities, which can be reduced at the working electrode. The protective electrode usually operates reductively. The individual electrodes arranged in the gas sensor are usually separated from one another by means of separator layers (so-called separators=ion-permeable membranes).

The inventor has surprisingly found that the long-term resistance to gas exposure and hence the long-term signal stability could be improved considerably in case of simultaneous addition of a boron compound and of an absorbent. The electrochemical gas sensor according to the present invention has a substantially improved long-term signal stability compared to the gas sensors known from the state of the art, especially in case of the determination of the concentrations of halogen-containing gases, above all in case of HF, and over a time period of at least 12 months to 18 months, especially in case of the determination of the concentrations of acid gases, i.e., of gases and/or vapors that have a pH value lower than 7 in an aqueous solution.

Another object of the present invention is to provide a process for determining the concentration of an acid analyte gas, with which a high long-term signal stability is guaranteed over a long time period. An acid analyte gas is admitted for this purpose to an electrochemical gas sensor, wherein the analyte gas diffuses through an opening at least partially to the working electrode and is reduced electrochemically at this working electrode. The reaction products (ions) formed in the process migrate at least partially to the counterelectrode, where they are oxidized again at least partially to an oxidation product. The analyte gas having diffused into the electrochemical gas sensor reacts chemically at least partially with a boron compound, especially boric acid and/or boron trioxide, which is preferably arranged on a separator layer (nonwoven) as a carrier between the working electrode and the counterelectrode. The oxidation product is absorbed at least partially by an absorbent or is bound chemically. The absorbent is preferably arranged at the counterelectrode.

The electrochemical gas sensor according to the present invention can be used for determining the concentrations of acid gases and/or acid gas mixtures or of acid vapors.

The advantages of the electrochemical gas sensor according to the present invention as well as the possible configuration thereof will be shown below on the basis of the following figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
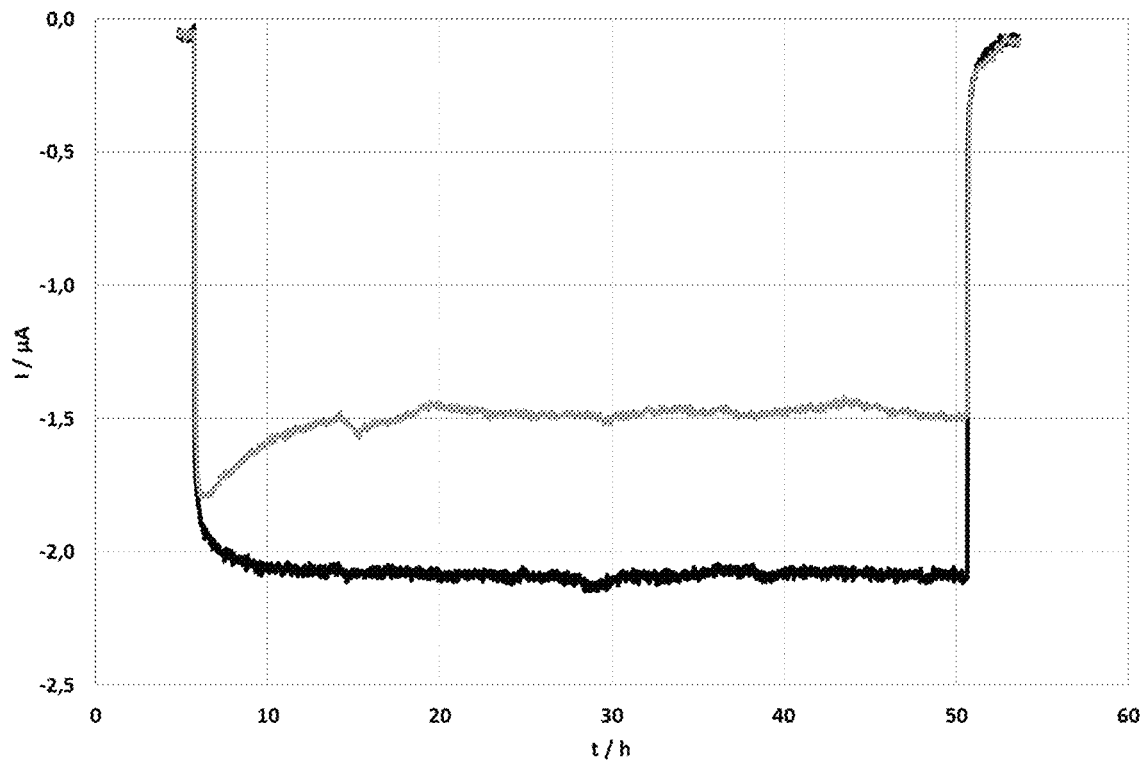
FIG. 1 is a comparison view showing measured signals of a gas sensor according to the present invention compared to a gas sensor known from the state of the art on exposure to HF as the analyte gas.

Referring to the drawings, FIG. 1 shows a comparison of the measured signals between an electrochemical gas sensor according to the present invention (black line) with an electrochemical gas sensor known from the state of the art (grey line) for identical experimental setups. The current intensity in $\mu A$ is plotted over the time in hours.

The electrochemical gas sensor according to the present invention additionally has a separator layer (polymer nonwoven carrying boric acid) between the working electrode and the counterelectrode. Both gas sensors were exposed first to air and then to 4.4 ppm of hydrogen fluoride as an analyte gas for 45 hours. The upper signal, which is not according to the present invention, shows the measured signal of a gas sensor known from the state of the art, whereas the lower signal shows the measured signal of the electrochemical gas sensor according to the present invention. It can clearly be seen that the grey line of the gas sensor known from the state of the art already "drops" to about 1.5 $\mu A$ after a short gas exposure time at a current intensity of about 1.75 $\mu A$ ($\mu A$) and the measured signal then remains relatively constant at 1.5 $\mu A$ with slight upward and downward movements of the measured signal until the end of the gas exposure after 45 hours. The black line of the gas sensor according to the present invention shows, by contrast, no comparable drop of the current intensity. The measured signal of the electrochemical gas sensor according to the present invention rather remains stable at about 2 $\mu A$ over the entire measurement time period, and, in particular, no "drops" of the measured signal are seen, unlike in case of the gas sensor not according to the present invention.

Figure 2:
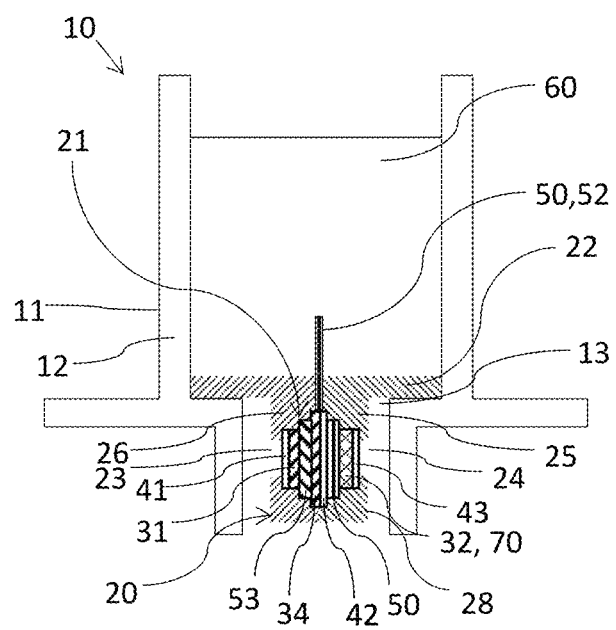
FIG. 2 is a schematic sectional view showing a configuration of an electrochemical gas sensor according to the present invention.

The gas sensor 10 according to the present invention shown in FIG. 2 comprises a housing 11 and an electrolyte reservoir 12 for an electrolyte 60, which encloses a reaction space 21. The electrode carrier 20 is fixed in a receiving structure 13 of the electrolyte reservoir 12 with the fastening section 22. The reaction space 21 is defined by a first wall section 25 and a second wall section 26 of the electrode carrier 20. The electrode carrier 20 has an inner surface and an outer surface 28. A first recess 23 and a second recess 24 are formed in the housing 11. The first recess 23 is a gas inlet, through which the analyte gas can diffuse into the reaction space 21. The second recess 24 is a gas outlet, through which gas formed at the counterelectrode 32 can diffuse from the reaction space 21. The working electrode 31 and the counterelectrode 32 of the gas sensor 10 are arranged in the reaction space 21. A hydrophilic, electrolyte-permeable separator layer 50 is located between the working electrode 31 and the counterelectrode 32. The working electrode 31 is covered towards the first recess 23 by a hydrophobic membrane 41. The separator layer 53, which contains boric acid, is arranged between the working electrode 31 and the protective electrode 34. The protective electrode 34 is separated along the diffusion path from the first recess 23 to the second recess 24 from the counterelectrode 32 by the membrane 42 and by the hydrophilic, electrolyte-permeable separator layer 50. The counterelectrode 32 is used as the carrier for the absorbent 70 and is covered in the direction of the second recess 24 by the hydrophobic membrane 43. In another embodiment, not shown, a reference electrode 33 is additionally arranged in the reaction space 21.

Figure 3:
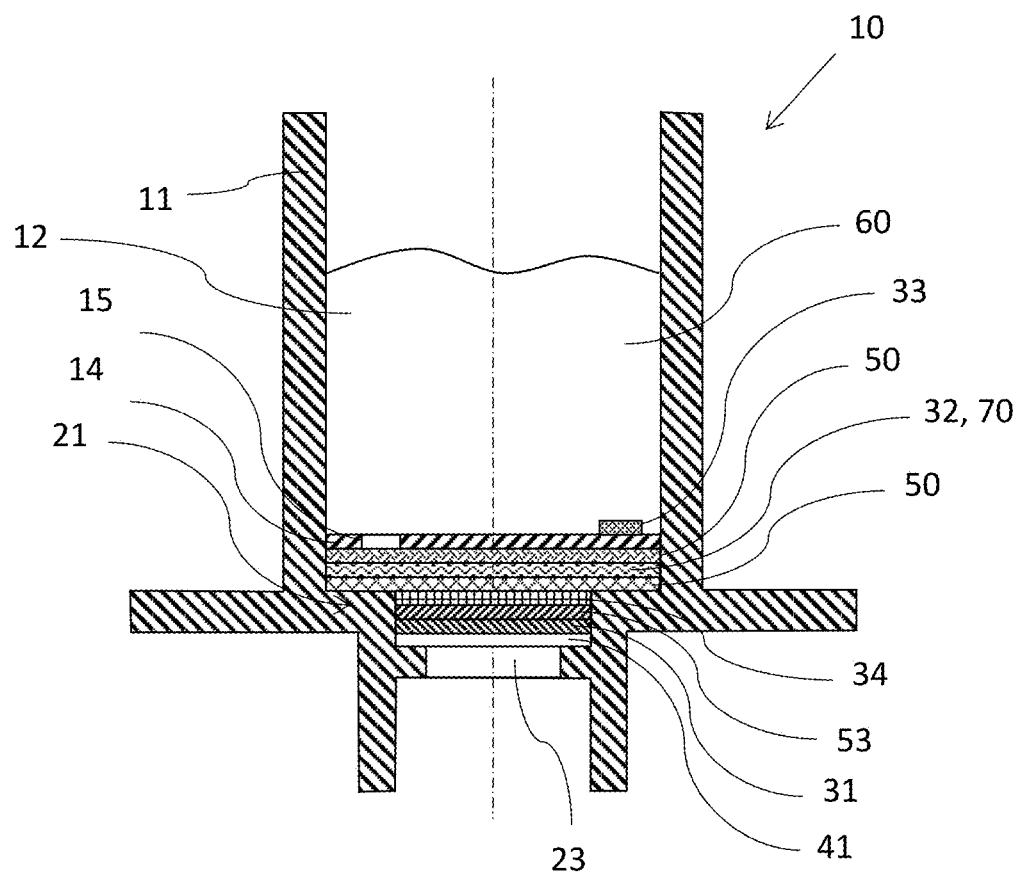
FIG. 3 is sectional view showing an alternative configuration with sensor structures rotated essentially by 90° in relation to the configuration of FIG. 2.

The arrangement of the electrodes 31, 32 and the first recess 23 as well as of the separator layers located between the electrodes and of the membranes covering the electrodes 31, 32 are rotated by 90° in the gas sensor 10 shown in FIG. 3 as compared to the gas sensor whose configuration is shown in FIG. 2. Further, a reference electrode 33 is arranged in the housing 11. The analyte gas reaches the working electrode 31 through the first recess 23 and the membrane 41. The separator layer 53 containing the boric acid is arranged behind the working electrode 31. In the direction of the diffusion path from the first recess 23 in the direction of the electrolyte-permeable opening 15, which is arranged in an electrolyte-impermeable separator layer 14, the separator layer 53 containing the boric acid is followed by the protective electrode 34 and then by the counterelectrode 32, which is enclosed by the separator layers 50 and acts as a carrier for absorbent 70.

While specific embodiments of the invention have been shown and described in detail to illustrate the application of the principles of the invention, it will be understood that the invention may be embodied otherwise without departing from such principles.

LIST OF REFERENCE NUMBERS

10 Gas sensor
11 Housing
12 Electrolyte reservoir
13 Receiving structure
14 Electrolyte-impermeable separator layer
15 Electrolyte-permeable opening
20 Electrode carrier
21 Reaction space
22 Fastening section
23 Recess
24 Recess
25 Wall section
26 Wall section
28 Surface
31 Working electrode
32 Counterelectrode
33 Reference electrode
34 Protective electrode
41 Hydrophobic membrane
42 Membrane
43 Hydrophobic membrane
50 Hydrophilic, electrolyte-permeable separator layer
52 Section
53 Separator layer containing boric acid
60 Electrolyte
70 Absorbent

What is claimed is:

1. An electrochemical gas sensor for an analyte gas, which analyte gas has a pH value lower than 7 in an aqueous solution, the gas sensor comprising:
    a housing;
    a working electrode arranged within the housing;
    a counter-electrode arranged within the housing;
    an electrolyte in the housing in conductive contact with the working electrode and with the counter-electrode;
    an absorbent in the housing for absorbing during use of the gas sensor a reaction product formed at the working electrode or at the counter- electrode or at the working electrode and at the counter-electrode; and
    at least one boron compound in the housing for reacting chemically with the analyte gas, wherein the boron compound is located in or on a separator layer and the separator layer is arranged between the working electrode and the counter-electrode, the boron compound comprising boric acid or boron trioxide or boric acid and boron trioxide.

2. The gas sensor in accordance with claim 1, wherein the boron compound consists of boric acid or boron trioxide or boric acid and boron trioxide.

3. The gas sensor in accordance with claim 1, wherein the boron compound is provided in the housing in at least one of: a powdered form; on a nonwoven carrier.

4. The gas sensor in accordance with claim 1, wherein the analyte gas contains one or more of halogen and $H_2S$ and acetic acid.

5. The gas sensor in accordance with claim 4, wherein the analyte gas contains one or more of hydrofluoric acid and hydrochloric acid and hydrogen bromide and hydrogen iodide.

6. The gas sensor in accordance with claim 1, wherein the absorbent is arranged at least partially at the working electrode or partially at the counter-electrode or partially at the working electrode and partially at the counter-electrode.

7. The gas sensor in accordance with claim 1, wherein the absorbent comprises a carbonate compound.

8. The gas sensor in accordance with claim 7, wherein the absorbent comprises an alkali carbonate compound or an alkaline earth carbonate component.

9. The gas sensor in accordance with claim 8, wherein the absorbent comprises one or more of $BaCO_3$ and $CaCO_3$.

10. The gas sensor in accordance with claim 1, wherein the working electrode comprises an electrode material selected from the group comprising carbon nanotubes, graphene, diamond-like carbon, and reduced graphene oxide.

11. The gas sensor in accordance with claim 1, wherein the counter-electrode comprises an electrode material selected from the group comprising carbon fibers, graphene, glassy carbon, and carbon nanotubes.

12. The gas sensor in accordance with claim 1, further comprising a reference electrode or a protective electrode or a reference electrode and a protective electrode.

13. The gas sensor in accordance with claim 1, wherein the electrolyte comprises an organic solvent and a conductive salt.

14. The gas sensor in accordance with claim 13, wherein the organic solvent contains a quinoid system, and the conductive salt has an organic cation.

15. A process for determining a concentration of an analyte gas, wherein the analyte gas has a pH value lower than 7 in an aqueous solution, wherein the process comprises the steps of:
    providing a gas sensor comprising: a housing; a working electrode arranged within the housing; a counter-electrode arranged within the housing; an electrolyte in the housing in conductive contact with the working electrode and with the counter-electrode; an absorbent in the housing for absorbing during use of the gas sensor a reaction product formed at the working electrode or at the counter-electrode or at the working electrode and at the counter-electrode; at least one boron compound in the housing for reacting chemically with the analyte gas;
    admitting the analyte gas to the electrochemical gas sensor;

at least partially reducing the analyte gas at the working electrode, wherein at least one reaction product migrates to the counter-electrode;

at least partially oxidating the reaction product at the counter-electrode into at least one oxidation product;

at least partially chemically reacting the analyte gas with the boron compound; and at least partially absorbing the oxidation product by the absorbent, wherein absorbing is by reaction with the absorbent, wherein the boron compound is located in or on a separator layer and the separator layer is arranged between the working electrode and the counter-electrode, the boron compound comprising boric acid or boron trioxide or boric acid and boron trioxide.

16. The process according to claim 15, further comprising determining, with the electrochemical gas sensor, concentrations of acid gases or concentrations of gas mixtures containing acid gases or concentrations of acid gases and gas mixtures containing acid gases.

17. The process according to claim 16, wherein concentrations of hydrofluoric acid are determined.

* * * * *